United States Patent
Park et al.

(10) Patent No.: US 10,835,497 B2
(45) Date of Patent: Nov. 17, 2020

(54) RIVASTIGMINE-CONTAINING SUSTAINED-RELEASE PHARMACEUTICAL COMPOSITION

(71) Applicant: NAVIPHARM CO., LTD., Suwon-si (KR)

(72) Inventors: Sang Geun Park, Suwon-si (KR); Hye Gyeong Shin, Suwon-si (KR); Jeong Woo Bae, Suwon-si (KR); Hyun Ju Choi, Seongnam-si (KR)

(73) Assignee: NAVIPHARM CO., LTD., Suwon-si (KR)

( * ) Notice: Subject to any disclaimer, the term of this patent is extended or adjusted under 35 U.S.C. 154(b) by 0 days.

(21) Appl. No.: 15/569,693

(22) PCT Filed: Apr. 27, 2016

(86) PCT No.: PCT/KR2016/004380
§ 371 (c)(1),
(2) Date: Oct. 26, 2017

(87) PCT Pub. No.: WO2016/175546
PCT Pub. Date: Nov. 3, 2016

(65) Prior Publication Data
US 2018/0125785 A1 May 10, 2018

(30) Foreign Application Priority Data
Apr. 27, 2015 (KR) .................. 10-2015-0058759

(51) Int. Cl.
| | |
|---|---|
| *A61K 9/16* | (2006.01) |
| *A61K 31/27* | (2006.01) |
| *A61K 9/50* | (2006.01) |
| *A61K 9/20* | (2006.01) |
| *A61K 47/32* | (2006.01) |
| *A61K 47/38* | (2006.01) |

(52) U.S. Cl.
CPC .......... *A61K 9/1652* (2013.01); *A61K 9/1635* (2013.01); *A61K 9/2077* (2013.01); *A61K 9/5026* (2013.01); *A61K 9/5073* (2013.01); *A61K 9/5078* (2013.01); *A61K 31/27* (2013.01); *A61K 47/32* (2013.01); *A61K 47/38* (2013.01)

(58) Field of Classification Search
None
See application file for complete search history.

(56) References Cited

U.S. PATENT DOCUMENTS

| 6,565,883 B2 | 5/2003 | Ogorka et al. |
|---|---|---|
| 8,846,100 B2 | 9/2014 | Shojaei et al. |
| 2005/0163847 A1* | 7/2005 | Cheng .................. A61K 9/2081 424/472 |
| 2007/0264323 A1* | 11/2007 | Shojaei ................ A61K 9/1676 424/451 |
| 2009/0317473 A1 | 12/2009 | Naringrekar et al. |
| 2010/0159001 A1 | 6/2010 | Cardinal et al. |
| 2010/0166864 A1* | 7/2010 | Gadre .................... A61K 9/209 424/486 |
| 2016/0008285 A1 | 1/2016 | Kidane et al. |

FOREIGN PATENT DOCUMENTS

| EA | 201190063 A1 | 2/2012 |
|---|---|---|
| JP | 2003-507416 A | 2/2003 |
| JP | 2012-512896 A | 6/2012 |
| JP | 2013-523757 A | 6/2013 |
| KR | 10-0603900 B1 | 7/2006 |
| KR | 10-0661441 B1 | 12/2006 |
| KR | 10-2007-0086667 A | 8/2007 |
| KR | 10-2012-0083276 A | 7/2012 |
| KR | 10-2014-0113542 A | 9/2014 |
| RU | 2390354 C2 | 5/2010 |
| WO | 01/13898 A2 | 3/2001 |
| WO | 2007-133203 A1 | 11/2007 |

OTHER PUBLICATIONS

International Search Report issued for International Application No. PCT/KR2016/004380 dated Sep. 30, 2016, 7 pages.
Extended European Search Report issued for European Patent Application No. 16786732.4 dated Nov. 20, 2018, 6 pages.

* cited by examiner

*Primary Examiner* — Katherine Peebles
(74) *Attorney, Agent, or Firm* — Rothwell, Figg, Ernst & Manbeck, P.C.

(57) ABSTRACT

The present invention relates to a rivastigmine-containing sustained-release pharmaceutical composition and, more specifically, to a rivastigmine-containing sustained-release pharmaceutical composition, which is a sustained-release preparation containing a pH-dependent delayed release phase, wherein, by controlling the release of the pharmaceutical composition to be minimized in the stomach at the initial stage of administration, the pharmaceutical composition can lower the maximum blood concentration (Cmax) compared with existing products while arriving at an effective blood concentration, thereby reducing side effects, and thereafter, maintaining the effective blood concentration through the sustained-release of main ingredients. As a result, the pharmaceutical composition according to the present invention exhibits the same effect as in the existing twice-a-day dosing through only the once-a-day dosing, and can increase the treatment efficiency of patients through the improvement in the convenience of administration of patients.

6 Claims, No Drawings

RIVASTIGMINE-CONTAINING SUSTAINED-RELEASE PHARMACEUTICAL COMPOSITION

CROSS-REFERENCE TO RELATED APPLICATION(S)

This application is a 35 U.S.C. 371 National Phase Entry Application from PCT/KR2016/004380, filed Apr. 27, 2016, which claims the benefit of Korean Patent Application No. 10-2015-0058759 filed on Apr. 27, 2015 with the Korean Intellectual Property Office, the disclosure of which is herein incorporated by reference in its entirety.

TECHNICAL FIELD

The present invention relates to a rivastigmine-containing sustained-release pharmaceutical composition and, more specifically, to a rivastigmine-containing sustained-release pharmaceutical composition, wherein the composition is a sustained-release preparation containing a pH-dependent delayed-release formulation, and wherein the preparation allows the sustained release of a main ingredient while passing through the gastrointestinal tract after ingestion to ensure an effective blood concentration, thereby exhibiting the same effect as in an existing twice-a-day regimen despite being ingested once-a-day.

BACKGROUND ART

In general, rivastigmine is a medicine for mild to moderate Alzheimer's dementia and Parkinson's dementia, and is administered at a dose of 1.5-6 mg twice a day. This medicine has been known to be mainly metabolized by esterase (e.g., acetyl and butyrylcholinesterase) and to have a half-life in the blood of 1 hour. However, such a short half-life in the blood makes it difficult to develop a sustained-release preparation for a once-a-day regimen. In addition, this medicine on the current market also has a problem in that the medicine frequently causes gastrointestinal side effects due to a high maximum blood concentration ($C_{max}$) at the initial stage caused by rapid release.

In the past, studies of the sustained release using a polymer matrix system were widely conducted to solve the above problems of medicines. However, the polymer matrix system has difficulty in controlling the initial release amount of a drug with high solubility in water, such as rivastigmine, and is not appropriate for continuously releasing a certain amount of a drug due to a phenomenon in which the release amount of a drug is relatively low in the later part. In addition, Korean Patent Application No. 2012-7003314 discloses a sustained-release preparation having both immediate-release and sustained-release properties, but the side effects due to a high blood concentration at the initial stage are still worrisome, and a long-term sustained-release for a once-a-day regimen is impossible.

Korean Patent Nos. 603900 or 661441 discloses a time-controlled sustained-release preparation containing rivastigmine, but the time-controlled sustained-release preparation using a semi-permeable membrane releases a time-controlled drug at the same time after a predetermined period of time, and thus, side effects thereof at the corresponding time are still problematic. As such, a rivastigmine preparation for a once-a-day regimen has not yet been developed, and the need for additional development for such a preparation is urgent.

DETAILED DESCRIPTION OF THE INVENTION

Technical Problem

An aspect of the present invention is directed to the sustained release of a hydrophilic medicine, such as rivastigmine, having high solubility in water, wherein a pH-dependent delayed-release formulation is prepared, and then is included together with or separately from a sustained-release formulation in a single preparation, thereby minimizing drug release in the stomach at the initial stage after drug ingestion and maintaining uniform release and absorption of an active ingredient for a long time while passing through the small intestine and large intestine. Thus, an aspect of the present invention is to provide a rivastigmine sustained-release pharmaceutical composition for a once-a-day regimen, wherein side effects of the drug are minimized by lowering the maximum blood concentration ($C_{max}$) through controlled release in the stomach at the initial stage, and thereafter, the effective blood concentration is maintained through the sustained release.

Technical Solution

In accordance with an aspect of the present invention, there is provided a rivastigmine-containing sustained-release pharmaceutical composition for a once-a-day regimen, the pharmaceutical composition including a pH-dependent delayed-release formulation.

The pH-dependent delayed-release formulation may contain a polymer having a property of being dissolved at pH 5.0 or higher and may be manufactured into a granule, pellet, or core tablet form.

The polymer having a property of being dissolved only at pH 5.0 or higher may be at least one selected from the group consisting of an acrylic acid-based copolymer, hydroxypropylmethylcellulose phthalate, and cellulose acetate phthalate, and a mixture thereof.

The pH-dependent delayed-release formulation may contain 25-90 wt % of rivastigmine in the total content of rivastigmine.

The pharmaceutical composition may further include a pH-independent sustained-release base inside the pH-dependent delayed-release formulation.

The pharmaceutical composition may include a pH-independent sustained-release formulation together with or separately from the pH-dependent delayed-release formulation.

The pH-independent sustained-release formulation may be contained in a matrix, granule, or a pellet form.

The pH-independent sustained-release formulation may include 10-75 wt % of rivastigmine in the total content of rivastigmine.

In the pharmaceutical composition, rivastigmine may be released in a content of, relative to the total content of rivastigmine, equal to or more than 10 wt and less than 40 wt % within 120 minutes, equal to or more than 40 wt % and less than 70 wt % within 6 hours, and equal to or more than 70 wt % within 12 hours.

Hereinafter, the present invention will be described in detail.

The present invention is directed to a rivastigmine sustained-release pharmaceutical composition containing a pH-dependent delayed-release formulation, and the pharmaceutical composition of the present invention may be implemented by preparing a delayed-release formulation composed of granules or pellets coated with a pH-dependent polymer, specifically, a polymer having a property of being dissolved at pH 5.0 or higher, and then including the prepared delayed-release formulation inside a sustained-release matrix or formulating the prepared delayed-release formulation together with sustained-release granules or pellets in a dosage form of a single tablet or a hard capsule.

In the pharmaceutical composition according to the present invention, the drug efficacy is expressed at the initial stage such that rivastigmine contained in the sustained-release formulation is slowly released to reach the minimum effective blood concentration, and thereafter, in the small intestine and large intestine showing pH 5.0 or higher, rivastigmine of the pH-dependent delayed-release formulation, together with rivastigmine of the sustained-release formulation, is additionally slowly released, thereby maintaining the uniform release throughout the gastrointestinal tract.

Here, the pH-dependent delayed-release formulation according to the present invention may be prepared as granules or pellets coated with a pH-dependent polymer, specifically, a polymer having a property of being dissolved at pH 5.0 or higher. Specifically, a rivastigmine coating liquid is sprayed on an inert core to form a main coating layer, and then a coating liquid containing a pH-dependent polymer is sprayed thereon to form a delayed-release coating layer, thereby delaying the release of the drug.

The inert core is preferably a spherical particle having a uniform size of 100-300 μm in diameter and composed of microcrystalline cellulose, lactose, white sugar, dextrin, and a mixture thereof. The inert core may be contained in a weight percent of 10-60% relative to the total weight of granules or pellets. The main ingredient coating layer may be prepared by dissolving rivastigmine and a binder in a suitable solvent and then spraying the mixture on the inert core. As a suitable binder, hydroxypropyl methylcellulose, hydroxypropyl cellulose, ethylcellulose, polyvinyl pyrrolidone, polyvinyl alcohol, Eudragit, and a mixture thereof may be used, and these may be used in a weight percent of 0.1-20.0% relative to rivastigmine used in the coating layer. As a suitable solvent, water, ethanol, isopropyl alcohol, acetone, methylene chloride, and a mixed solvent thereof may be used. An appropriate plasticizer and lubricant may be further used to facilitate the process. As a suitable plasticizer, polyethylene glycol, triethyl citrate, triacetin, dialkyl sebacate, diethyl phthalate, and the like may be used, and as a suitable lubricant, talc, glycerol monostearate, colloidal silicon dioxide, and the like may be used, but are not limited thereto.

With respect to still another method for forming granules containing a main ingredient, a binder liquid is added to a mixture containing a main ingredient and appropriate pharmaceutical excipients to prepare a kneaded product, which is then passed through a sieve of an extruder, thereby preparing cylindrical granules, and then cylindrical granules are finally manufactured into spherical granules using a spheronizer.

The pH-dependent delayed-release formulation of the present invention may be completed by adding a pH-dependent delayed coating layer to the spherical main ingredient granules, which have been prepared through spraying or extrusion. The pH-dependent delayed coating layer may be formed by using a coating material having a property of being dissolved only at pH 5.0 or higher, that is, an acrylic acid-based copolymer, hydroxypropyl methylcellulose phthalate, cellulose acetate phthalate, and a mixture thereof. Especially, as the acrylic acid-based copolymer, Eudragit L100-55, Eudragit L100, Eudragit S100, and a mixture or aqueous dispersion thereof may be used, but is not limited thereto. These polymers may be used in the form of being dissolved or dispersed together with an appropriate plasticizer and lubricant in a solvent. Alternatively, a product containing the polymer together with a plasticizer and a lubricant, such as Acryl-Eze, may be used. The pH-dependent delayed coating layer may be used in a weight percent of 10-100%, and preferably, 30-60%, relative to the weight of granules containing a main ingredient or a main ingredient coating layer. If the pH-dependent delayed coating layer is used in a weight percent of less than 10%, the initial release of the main ingredient cannot be controlled. If 100% or more, the time required for dissolving the pH-dependent coating layer is long, resulting in an excessive delay effect.

The pH-dependent delayed-release formulation may be added with sustained-release characteristics to control the release of the drug from granulate. In cases of preparing the main ingredient coating layer and extrusion type main ingredient granules, the release of the drug can be controlled by containing a highly viscous polymer, and can be controlled by coating the prepared spherical granules with a pH-independent sustained-release base. Here, ethylcellulose, methylcellulose, an acrylic acid-based copolymer, hydroxypropyl methylcellulose, and the like may be used. Preferably, the use of a water-insoluble polymer, such as ethylcellulose, may be used, and a commercially sold ethylcellulose aqueous dispersion (Surelease) may be used. The sustained-release base may be used in a weight percent of 3-60% relative to the main ingredient granules. The sustained-release base has an effect of shortening the time required for a process by reducing the use amount of the pH-dependent delayed-release formulation, and can assist to keep the constant release of the drug by controlling the release of the drug at the same time after the pH-dependent coating layer is dissolved.

Such a pH-dependent delayed-release formulation suppresses the release in the stomach, thereby minimizing side effects occurring due to the release of a high amount of rivastigmine at the initial stage, and thereafter, allows the sustained-release during a long retention time in an alkali environment, such as the small intestine and large intestine, thereby further extending the time of drug release. However, the excessive control of the amount of drug release in the stomach may delay the time to reach an effective blood concentration, and especially, is not appropriate for patients with a relatively long retention time in the stomach. As a way to compensate for these defects, the present invention may contain an additional independent sustained-release formulation. The sustained-release formulation is pH-independent, and may be contained in the form of a matrix or separate granules or pellets.

As for a method for preparing a pharmaceutical composition to include both a pH-dependent delayed release formulation and a sustained-release formulation in the present invention, granules or pellets formed as the pH-dependent delayed-release formulation are mixed in a matrix form of the sustained-release formulation containing a predetermined amount of rivastigmine, and the mixture is manufactured as a tablet; or the pH-dependent delayed release formulation together with a separate granule or pellet type sustained-release formulation is compressed to obtain a tablet or is loaded in a hard capsule to obtain a capsule dosage form.

The sustained-release matrix may be prepared by uniformly containing predetermined amounts of rivastigmine and pH-dependent delayed-release formulation in a network using a hydrophilic and water-insoluble sustained-release base. As the sustained-release base, hydroxypropyl methylcellulose, ethylcellulose, hydroxyethyl cellulose, a carbomer, a polyvinyl pyrrolidone-vinyl acetate copolymer, and a mixture thereof may be used. Ordinary pharmaceutical excipients are added to the sustained-release base to prepare a mixture for direct tableting or granules through a process, such as wet granulation or dry granulation, and the mixture or granules are manufactured into a tablet through compression. The sustained-release formulation through these sustained-release bases is prepared such that the amount of drug release is constant without any difference depending on the pH of the gastrointestinal tract, and only the release rate of the drug can be controlled depending on the use amount of the sustained-release base, and therefore, the release of the drug can be initiated even in the stomach with low pH.

In addition, the sustained-release formulation may be manufactured into granules and pellets in the form independent from a pH-dependent delayed-release formulation, and the granules and pellets may be manufactured using an ordinary sustained-release base and pharmaceutically acceptable excipients by wet granulation, dry granulation, fluidized bed granulation, and fluidized bed coating. An independent form of sustained-release formulation may be manufactured into a capsule dosage form by being loaded together with a pH-dependent delayed-release formulation in a hard capsule, or may be manufactured into a general tablet, multi-layered tablet, and press-coated tablet form by additionally mixing ordinary additives, such as an excipient, a diluent, a lubricant, a stabilizer, or a binder.

The content of rivastigmine of the sustained-release formulation of the present invention contains, relative to the total content of the main ingredient, preferably 10-75 wt %, more preferably 10-50 wt %, and most preferably 15-35 wt % of a main ingredient. The main ingredient is slowly, but not immediately, released from the sustained-release formulation, and thus the amount of initial release can be controlled at a predetermined amount, and when compared with conventional ordinary tablets, the maximum blood concentration ($C_{max}$) can be reduced, thereby reducing gastrointestinal side effects.

Last, in the pharmaceutical composition according to the present invention, the main ingredient is released in a content of, relative to the total content thereof, equal to or more than 10 wt % and less than 40 wt % within 120 minutes, equal to or more than 40 wt % and less than 70 wt % within 6 hours, and equal to or more than 70 wt % within 12 hours. If the main ingredient is released in the stomach in a content exceeding 40 wt % relative to the total content thereof within 120 minutes of initial release, gastrointestinal side effects due to the excessive release of the main ingredient may still occur, and if released in a content of less than 10 wt %, the initial effective blood concentration is difficult to reach and thus efficacy is delayed. Thereafter, a predetermined amount of rivastigmine is sustainedly released to keep the effective blood concentration, and within 12 hours, rivastigmine needs to be released in a content of 70% or more relative to the total content thereof and otherwise, the bioavailability of the administered drug may be lowered. Thus, setting such standards is necessary.

Advantageous Effects

The present invention is directed to a rivastigmine-containing sustained-release pharmaceutical composition, and the pharmaceutical composition according to the present invention minimizes the release of a drug from the pH-dependent delayed-release formulation in the stomach with low pH at the initial stage and slowly releases only the drug of the sustained-release formulation, thereby controlling the initial release of a hydrophilic drug, such as rivastigmine, showing high solubility in water, thus reducing gastrointestinal side effects due to a high maximum blood concentration ($C_{max}$) of a conventional ordinary preparation and allowing the drug to reach to an effective blood concentration. Thereafter, the amount of rivastigmine released from the sustained-release formulation is continuously reduced in the small intestine and large intestine, and in addition to this, rivastigmine is continuously released from the pH-dependent delayed-release formulation for 12 hours so that the effective blood concentration of the main ingredient can be continuously maintained. The present invention allows a once-a-day regimen of a drug with high solubility in water and a very short half-life in the blood, and can also improve the treatment effect through the improvement in the ease and compliance of administration of a patient.

BEST MODE FOR CARRYING OUT THE INVENTION

Hereinafter, preferable examples and test examples will be set forth for better understanding of the present invention. However, the following examples and test examples are merely provided to make it easier to understand the present invention, but the scope of the present invention is not limited by these examples and test examples.

Example 1

After 400 g of Cellets 100 (180-250 µm) was fluidized in a fluidized bed coater, a coating liquid obtained by adding 192 g of rivastigmine tartrate, 20 g of hydroxypropylmethylcellulose (Methocel E5), and 138 g of talc to a mixed solvent of ethanol and purified water was sprayed in a bottom spray manner to coat a drug layer thereon. A coating liquid obtained by dispersing 1,080 g of Surelease (ethylcellulose aqueous dispersion) together with 100 g of talc in purified water was sprayed thereon to add a sustained-release layer. A coating liquid obtained by dispersing 560 g of Acryl-Eze made of pH-dependent polymer Eudragit L100-55 in purified water was sprayed on the formed spherical granules in a bottom spray manner to add a pH-dependent coating layer thereon. The granules thus prepared contained 9.6 mg of rivastigmine tartrate relative to a standard weight of 84 mg.

Separately, 14.4 g of rivastigmine tartrate, 484.2 g of microcrystalline cellulose (Vivapur 12), 157.5 g of hydroxypropyl methylcellulose 2208 (Methocel K100M), 5.4 g of aluminum magnesium silicate (Cab-O-Sil), and 10.5 g of magnesium stearate were mixed, followed by compression in a roller compactor and sizing, to prepare sustained-release dry granules.

Then, 378.0 g of the prepared pH-dependent delayed-release granules (containing 43.2 g of rivastigmine tartrate) and 672.0 g of the sustained-release dry granules (containing 14.4 g of rivastigmine tartrate) were mixed, and compressed to a weight of 350 mg per tablet in a rotary tableting machine, thereby manufacturing tablets. The rivastigmine tartrate was contained in a total of 19.2 mg per tablet, in which 14.4 mg of rivastigmine tartrate was contained in the pH-dependent delayed-release formulation and 4.8 mg of rivastigmine tartrate was contained in the sustained-release formulation.

Examples 2 and 3

In Examples 2 and 3, 3,000 tablets were manufactured by the same method as in Example 1, and here, the amounts of raw medicines followed table 1 below. In both Examples 2 and 3, rivastigmine tartarate was contained in a total of 19.2 mg per tablet. In Example 2, 9.6 mg of rivastigmine tartarate was contained in the pH-dependent delayed-release formulation and 9.6 mg of rivastigmine tartarate was contained in the sustained-release formulation. In Example 3, 4.8 mg of rivastigmine tartarate was contained in the pH-dependent delayed-release formulation and 14.4 mg of rivastigmine tartarate was contained in the sustained-release formulation.

TABLE 1

Amount of raw medicines (corresponding to 3,000 tablets, g) in Examples 1 to 3

| Raw medicines | Example 1 | Example 2 | Example 3 |
|---|---|---|---|
| pH-dependent delayed-release granules in Example 1 | 378.0 | 252.0 | 126.0 |
| Rivastigmine tartarate | 14.4 | 28.8 | 43.2 |
| Vivapur 12 | 484.2 | 595.8 | 707.4 |
| Methocel K100M | 157.5 | 157.5 | 157.5 |
| Cab-o-sil | 5.4 | 5.4 | 5.4 |
| Magnesium stearate | 10.5 | 10.5 | 10.5 |
| Total | 1,050.0 | 1,050.0 | 1,050.0 |

Example 4

After 400 g of Cellets 100 (180-250 µm) was fluidized in a fluidized bed coater, a coating liquid obtained by adding 192 g of rivastigmine tartarate, 20 g of hydroxypropyl methylcellulose (Methocel E5), and 108 g of talc to a mixed solvent of ethanol and purified water was sprayed in a bottom spray manner to coat a drug layer thereon. After the formed spherical granules were fluidized, a coating liquid obtained by dissolving 40 g of Opadry 03K19229 in a mixed solvent of ethanol and purified water was sprayed thereon to add a subcoating layer. Then, a coating liquid obtained by dispersing 780 g of Acryl-Eze composed of pH-dependent polymer Eudragit L100-55 in purified water was sprayed in a bottom spray manner to add a pH-dependent coating layer thereon. The granules thus prepared contained 9.6 mg of rivastigmine tartarate relative to a standard weight of 77 mg.

Separately, 5.76 g of rivastigmine tartarate, 402.54 g of microcrystalline cellulose (Vivapur 12), 210.0 g of hydroxypropyl methylcellulose 2208 (Methocel K100M), 5.4 g of aluminum magnesium silicate (Cab-O-Sil), and 10.5 g of magnesium stearate were mixed, followed by compression in a roller compactor and sizing, to prepare sustained-release dry granules.

Then, 415.8 g of the prepared pH-dependent delayed-release granules (containing 51.84 g of rivastigmine tartarate) and 634.2 g of the sustained-release dry granules (containing 5.76 g of rivastigmine tartarate) were mixed, and compressed to a weight of 350 mg per tablet in a rotary tableting machine, thereby manufacturing tablets. The rivastigmine tartarate was contained in a total of 19.2 mg per tablet, in which 17.28 mg of rivastigmine tartarate was contained in the pH-dependent delayed-release formulation and 1.92 mg of rivastigmine tartarate was contained in the sustained-release formulation.

Example 5

After 192 g of rivastigmine tartarate, 300 g of microcrystalline cellulose (Heweten 101), and 268 g of lactose hydrate (Pharmatose 200) were mixed, a binder obtained by dissolving 40 g of polyvinyl pyrrolidone (PVP K-30) in purified water was applied thereto, thereby preparing a kneaded product. The kneaded product was passed through an extruder to prepare cylindrical granules, which were then manufactured into spherical main ingredient granules using a spheronizer. The main ingredient granules were fluidized in a fluidized bed coater, and then a coating liquid obtained by dispersing 1,280 g of Surelease (ethyl cellulose aqueous dispersion) together with 80 g of talc in purified water was sprayed thereon in a bottom spray manner to add a sustained-release layer. A coating liquid obtained by dispersing 500 g of Acryl-Eze composed of pH-dependent polymer Eudragit L100-55 in purified water was sprayed on the formed spherical granules in a bottom spray manner to add a pH-dependent coating layer thereon. The granules thus prepared contained 9.6 mg of rivastigmine tartarate relative to a standard weight of 85 mg.

Separately, 14.4 g of rivastigmine tartarate, 479.7 g of microcrystalline cellulose (Vivapur 12), 157.5 g of hydroxypropylmethylcellulose 2208 (Methocel K100M), 5.4 g of aluminum magnesium silicate (Cab-O-Sil), and 10.5 g of magnesium stearate were mixed, followed by compression in a roller compactor and sizing, thereby manufacturing sustained-release formulation dry granules.

Then, 382.5 g of the prepared pH-dependent delayed-release granules (containing 43.2 g of rivastigmine tartarate) and 667.5 g of the sustained-release dry granules (containing 14.4 g of rivastigmine tartarate) were mixed, and compressed to a weight of 350 mg per tablet in a rotary tableting machine, thereby manufacturing tablets. The rivastigmine tartarate was contained in a total of 19.2 mg per tablet, in which 14.4 mg of rivastigmine tartarate was contained in the pH-dependent delayed-release formulation and 4.8 mg of rivastigmine tartarate was contained in the sustained-release formulation.

Example 6

After 500 g of Non-Pareil (300-425 µm) was fluidized in a fluidized bed coater, a coating liquid obtained by adding 96 g of rivastigmine tartarate, 10 g of hydroxypropyl methylcellulose (Methocel E5), and 34 g of talc to a mixed solvent of ethanol and purified water was sprayed in a bottom spray manner to coat a drug layer thereon. After the formed spherical granules were fluidized, a coating liquid obtained by dissolving 20 g of Opadry 03K19229 in a mixed solvent of ethanol and purified water was sprayed thereon to add a subcoating layer. Then, a coating liquid obtained by dispersing 800 g of Surelease (ethylcellulose aqueous dispersion) in purified water was sprayed to add a sustained-release layer, thereby manufacturing sustained-release pellets. The granules thus prepared contained 9.6 mg of rivastigmine tartarate relative to a standard weight of 102 mg. A coating liquid obtained by dispersing 400 g of Acryl-Eze composed of pH-dependent polymer Eudragit L100-55 in purified water was sprayed in a bottom spray manner in a fluidized bed coater to add a pH-dependent coating layer on the sustained-release pellets. The pH-dependent delayed release formulation pellets thus manufactured contained 9.6 mg of rivastigmine tartarate relative to a standard weight of 142 mg.

After 153 g of the sustained-release pellets and 639 g of the pH-dependent delayed-release pellets were mixed, the mixture was placed in a hard capsule to 264 mg per capsule. The rivastigmine tartarate was contained in a total of 19.2 mg per capsule, in which 14.4 mg of rivastigmine tartarate was contained in the pH-dependent delayed-release formulation and 4.8 mg of rivastigmine tartarate was contained in the sustained-release formulation.

Comparative Example 1

After 19.2 g of rivastigmine tartrate, 271.3 g of microcrystalline cellulose (Vivapur 12), 56.0 g of hydroxypropyl methylcellulose 2208 (Methocel K100M), and 3.5 g of magnesium stearate were mixed, the mixture was compressed to 350 mg per tablet, thereby manufacturing tablets. The rivastigmine tartarate was contained in a total of 19.2 mg per capsule.

Comparative Example 2

After 400 g of Cellets 100 (180-250 μm) was fluidized in a fluidized bed coater, a coating liquid obtained by adding 192 g of rivastigmine tartrate, 20 g of hydroxypropyl methylcellulose (Methocel E5), and 148 g of talc to a mixed solvent of ethanol and purified water was sprayed in a bottom spray manner to coat a drug layer thereon. After the formed spherical granules were fluidized, a coating liquid obtained by dissolving 40 g of Opadry 03K19229 in a mixed solvent of ethanol and purified water was sprayed thereon to add a subcoating layer. Then, a coating liquid obtained by dispersing 1,600 g of Surelease (ethylcellulose aqueous dispersion) together with 200 g of talc in purified water was sprayed thereon, thereby manufacturing sustained-release formulation not containing a pH-dependent polymer. The granules thus prepared contained 9.6 mg of rivastigmine tartarate relative to a standard weight of 70 mg.

Separately, 4.8 g of rivastigmine tartarate, 182.4 g of microcrystalline cellulose (Vivapur 12), 52.5 g of hydroxypropyl methylcellulose 2208 (Methocel K100M), 1.8 g of aluminum magnesium silicate (Cab-O-Sil), and 3.5 g of magnesium stearate were mixed, followed by compression in a roller compactor and sizing, to prepare sustained-release formulation dry granules.

Then, 105.0 g of the prepared sustained-release fluidized bed granules (containing 14.4 g of rivastigmine tartrate) and 245.0 g of the sustained-release dry granules (containing 4.8 g of rivastigmine tartrate) were mixed, and compressed to a weight of 350 mg per tablet in a rotary tableting machine, thereby manufacturing tablets. The rivastigmine tartarate was contained in a total of 19.2 mg per capsule.

Test Example 1

A tablet in each of the examples and comparative examples was subjected to a dissolution test in 750 mL of a dissolution solution of 0.1 N HCl at 37° C. under rotation conditions of 50 rpm by the paddle method. Two hours after the initiation of the dissolution test, the pH was changed by adding 250 mL of a 0.25 M tribasicphosphate buffer. At each sampling time, 5 mL was taken, and filtered with a membrane filter, and analyzed by liquid chromatography.

TABLE 2

| | Accumulative dissolution rate (%) of rivastigmine for each time | | | | | | | | | | |
|---|---|---|---|---|---|---|---|---|---|---|---|
| | Time (min) | | | | | | | | | | |
| | 0 | 15 | 30 | 60 | 120 | 240 | 360 | 480 | 600 | 720 | 840 |
| Example 1 | 0 | 4.9 | 8.3 | 13.6 | 23.6 | 37.9 | 47.3 | 56.4 | 64.9 | 74.0 | 82.6 |
| Example 2 | 0 | 5.2 | 9.6 | 16.0 | 28.9 | 42.5 | 54.0 | 63.1 | 73.0 | 81.5 | 92.3 |
| Example 3 | 0 | 9.0 | 14.0 | 22.6 | 35.7 | 50.7 | 62.9 | 71.6 | 81.6 | 91.8 | 99.8 |
| Comparative Example 1 | 0 | 14.0 | 23.8 | 39.1 | 56.8 | 72.3 | 81.8 | 89.0 | 94.9 | 99.7 | 99.9 |
| Comparative Example 2 | 0 | 13.9 | 21.0 | 31.0 | 44.9 | 61.2 | 72.8 | 82.2 | 90.2 | 96.2 | 99.8 |

Test Examples 2

Beagle dogs were administered with the tablets of Example 1, Example 3, and Comparative Example 1 and commercially available medicine Exelon capsule, and then blood concentration analysis was conducted. The beagle dogs used in the test were fasted from the day before administration for empty stomach, and then fed with one-third of the usual diet in the morning. After six beagles for each group were orally administered with one half of the tablet (9.6 mg of rivastigmine tartarate) in each of Example 1, Example 3, and Comparative Example 1 and an Exelon capsule (4.8 mg of rivastigmine tartrate), together with 30 ml of water. The blood was taken from the brachial vein of each of the beagles, and added in heparinized culture tube, followed by centrifugation (3000 rpm, 10 min), thereby separating plasma. Then, the blood concentration of rivastigmine was analyzed using LC/MS/MS.

TABLE 3

| Beagle dog PK parameter | | | | |
|---|---|---|---|---|
| | Example 1 | Example 3 | Comparative Example 1 | Exelon capsule |
| AUC | 20423.7 | 18566.4 | 16712.8 | 8137.1 |
| $C_{max}$ | 3254.8 | 4566.5 | 8850.6 | 4552.1 |
| $T_{max}$ | 1.4 | 1.5 | 1.4 | 2.1 |
| $t_{1/2}$ | 2.7 | 1.6 | 1.2 | 0.8 |

As a result of testing, Examples 1 and 3 administered with a total of rivastigmine tartarate of 9.6 mg showed about 2.5-fold and 2.3-fold AUC values compared with Exelon capsule administration (4.8 mg of rivastigmine tartarate), respectively, indicating sufficient bioavailability, but equivalent or lower maximum blood concentration ($C_{max}$) compared with Exelon capsule administration. Whereas, Comparative Example 1 not containing pH-dependent granules showed a two-fold AUC value compared with Exelon capsule, but about 1.9-fold maximum blood concentration ($C_{max}$), indicating that Exelon did not control the initial release amount.

The invention claimed is:

1. A rivastigmine-containing sustained-release pharmaceutical composition for a once-a-day regimen, the pharmaceutical composition comprising: a pH-dependent delayed-release formulation and a matrix form of a pH-independent sustained-release formulation, wherein the pH-dependent delayed-release formulation is in a granule form comprising a pH-dependent polymer having the property of being dissolved at pH 5.0 or higher and 25-90 wt % of rivastigmine relative to the total content of rivastigmine in the pharmaceutical composition, wherein the pH-independent sustained-release formulation comprises, inside the matrix form, the pH-dependent delayed release formulation and 10-75 wt % of rivastigmine relative to the total content of rivastigmine in the pharmaceutical composition, wherein the pH-dependent delayed-release formulation in the granule form comprises an inert core, a rivastigmine coating layer on the inert core and the pH-dependent polymer coated on the rivastigmine-coated core, and wherein the pharmaceutical composition is in a tablet form.

2. The pharmaceutical composition of claim 1, wherein the polymer is at least one selected from the group of an acrylic acid-based copolymer, hydroxypropylmethylcellulose phthalate, and cellulose acetate phthalate, and a mixture thereof.

3. The pharmaceutical composition of claim 1, wherein the pH-dependent delayed-release formulation further comprises a pH-independent sustained release base.

4. The pharmaceutical composition of claim 1, wherein rivastigmine is released in a content of, relative to the total content of rivastigmine in the pharmaceutical composition, equal to or more than 10 wt % and less than 40 wt % within 120 minutes, equal to or more than 40 wt % and less than 70 wt % within 6 hours, and equal to or more than 70 wt % within 12 hours, as measured in a dissolution test of the pharmaceutical composition initially in 750 mL of a dissolution solution of 0.1 N HCl at 37° C. under rotation conditions of 50 rpm by the paddle method, and followed by adding 250 mL of a 0.25 M tribasic phosphate buffer two hours after the initiation of the dissolution test.

5. The pharmaceutical composition of claim 1, wherein the inert core is a spherical particle having a uniform size of 100-300 μm in diameter.

6. The pharmaceutical composition of claim 3, wherein the pH-independent sustained-release base comprises ethylcellulose, methylcellulose, or hydroxypropyl methylcellulose.

* * * * *